United States Patent
Bell et al.

(10) Patent No.: US 8,255,354 B2
(45) Date of Patent: Aug. 28, 2012

(54) METHOD OF DETERMINING THE PROBABILITY THAT DATA IS ASSOCIATED WITH A SOURCE OF A PLURALITY OF SOURCES

(75) Inventors: Graham Bell, Hunters Hill (AU); Brynn Hibbert, Randwick (AU)

(73) Assignee: E-Nose Pty Ltd, Eveleigh (AU)

( * ) Notice: Subject to any disclaimer, the term of this patent is extended or adjusted under 35 U.S.C. 154(b) by 720 days.

(21) Appl. No.: 12/439,334

(22) PCT Filed: Aug. 23, 2007

(86) PCT No.: PCT/AU2007/001214
§ 371 (c)(1),
(2), (4) Date: Jun. 24, 2009

(87) PCT Pub. No.: WO2008/025059
PCT Pub. Date: Mar. 6, 2008

(65) Prior Publication Data
US 2010/0010956 A1    Jan. 14, 2010

(30) Foreign Application Priority Data

Aug. 28, 2006 (AU) ................ 2006904660
Jun. 19, 2007 (AU) ................ 2007903280

(51) Int. Cl.
*G06N 5/00* (2006.01)
(52) U.S. Cl. .......................... 706/52; 706/45
(58) Field of Classification Search .............. 706/52, 706/45
See application file for complete search history.

(56) References Cited

U.S. PATENT DOCUMENTS

| | | | |
|---|---|---|---|
| 5,416,724 A | 5/1995 | Savic | |
| 5,832,411 A | 11/1998 | Schatzmann et al. | |
| 6,456,491 B1* | 9/2002 | Flannery et al. | 361/679.33 |
| 6,496,742 B1 | 12/2002 | Labreche et al. | |
| 6,970,560 B1 | 11/2005 | Hench et al. | |
| 7,096,125 B2 | 8/2006 | Padmanabhan et al. | |

FOREIGN PATENT DOCUMENTS

EP    1065578    1/2001

OTHER PUBLICATIONS

Knuth, Bayesian Source Separation and Localization, SPIE'98 Proceedings: Bayesian Inference for Inverse Problems, SPIE vol. 3459, San Diego, Jul. 1998, pp. 147-158.*
International Search Report for International Application No. PCT/AU2007/001214, dated Sep. 25, 2007.

* cited by examiner

*Primary Examiner* — Wilbert L Starks
(74) *Attorney, Agent, or Firm* — Marshall, Gerstein & Borun LLP (57) ABSTRACT

The present invention provides a method and apparatus for determining the probability that sampled data, associated with a source and obtained from a plurality of data input sources, are from a known source, given prior observed data obtained by the plurality of data input sources for one or more known sources. In one embodiment the data input sources are sensors for detecting molecules conveyed though the air and the method comprises identifying a source of the molecules. The present invention also provides a method of determining information about the position of at least one sensor relative to a previously known type of source.

30 Claims, 6 Drawing Sheets

METHOD OF DETERMINING THE PROBABILITY THAT DATA IS ASSOCIATED WITH A SOURCE OF A PLURALITY OF SOURCES

FIELD OF THE INVENTION

The present invention relates to a method of determining the probability that data is associated with a source of a plurality of sources, in particular to a method of predicting the source of data sampled with an array of sensors.

BACKGROUND OF THE INVENTION

The Bayesian theory to discern different hypotheses when given experimental evidence (data) was developed by Rev. Thomas Bayes in 1763. Bayes' theorem allows calculation of the probability of an hypothesis $H_i$ based on available evidence E. This is written $Pr(H_i|E)$.

According to Bayes, for N competing and mutually exclusive hypotheses:

$$Pr(H_i | E) = \frac{PR(E | H_i)Pr(H_i)}{\sum_{j=1}^{N} Pr(E | H_j)Pr(H_j)} \quad (1)$$

where $Pr(H_i|E)$ is the probability of the hypothesis H given evidence E, and $Pr(H_i)$ is the prior probability (before any evidence) of the hypothesis and the sum is over all mutually exclusive hypotheses. The term $Pr(E|H_i)$ is either the probability of finding the evidence E given the truth of the hypothesis $H_i$, or the probability density function of the hypothesis $H_i$ at a value given by the evidence E (this is also known as the 'likelihood'). In the absence of any other prior knowledge of the system, each $Pr(H_i)$ can be set as 1/N, the so-called "flat prior".

The inventors of the present invention have applied Bayesian theory to develop a statistical tool for the treatment in real time of data from unknown sources which allows for comparison of the real time data with a template of previously recorded data from known sources in order to effect a decision with a given probability of the source of the real time data being generated by one of the known sources.

SUMMARY OF THE INVENTION

The present invention provides in a first aspect a method of determining the probability that sampled data, associated with a source and obtained from a plurality of data input sources, are from a known source, given prior observed data obtained by the plurality of data input sources for one or more known sources, the method comprising the steps of:
a) calculating probability density functions for each known source for the sampled data being associated with that source and/or calculating probability density functions for the sampled data being associated with none of the known sources using the data and the prior observed data;
b) calculating a first set of probabilities that the sampled data is associated with at least one of the known sources or none of the known sources using a predetermined prior probability and the probability density functions from step a); and
c) calculating a subsequent set of probabilities that the sampled data is associated with at least one of the known sources or none of the known sources using the probabilities calculated in the step b) and the probability density functions from step a) calculated from the sampled data.

In one embodiment of the invention, the method comprises repeating step c) for a further data set to calculate a further subsequent set of a plurality of probabilities.

In a further embodiment the method comprises iteratively repeating step c) to calculate further subsequent sets of pluralities of probabilities for a plurality of further data sets.

The further data set or the plurality of further data sets may be sampled prior, simultaneously or subsequently to the sampled data.

In one embodiment the data input source is a sensor. The plurality of sensors sample data from the source, each sensor being independent of the other sensors.

In an alternative embodiment the plurality of data input sources can correspond to data obtained from a spectrum, chromatogram or mass spectrum and so forth, optionally transformed to a single measure.

The method of the present invention typically relies on prior knowledge of a pattern of output data expected for each known source for a given sensor or data input source. It is desirable, therefore that sufficient observed data should have been previously acquired to capture substantially all possible variations in data values measured by the given sensor for the respective known source, such that the observed data is sufficiently representative of the known source.

In one embodiment of the invention, the prior observed data has been mathematically manipulated to reduce noise, adjust the baseline, or smooth the prior observed data using suitable filter routines.

In an alternative embodiment, the prior observed data can be mathematically manipulated according to a discriminating function that is expected to discriminate between known sources of the data (f(V)). For example, the data values observed with an array of sensors $V_1, V_2 \ldots V_{n-1}$ can be divided by the data values observed with sensor $V_n$. Other discriminating functions include, but are not limited to, logarithms of data values or performing a principal component analysis (PCA) and taking PC scores, or other linear or non-linear combinations of the data observed with the array of sensors. The number of discriminating functions may be less than or equal to the number of sensor outputs. For example, in the case where the data observed with the array of sensors $V_1, V_2 \ldots V_{n-1}$ can be divided by the data observed with sensor $V_n$, there are one fewer discriminating functions than data outputs.

Typically, the data associated with the source will undergo the same mathematical manipulation as the prior observed data to reduce noise, adjust the baseline for the sampled data, or smooth the data, and/or to obtain discriminating functions of the data as described above with respect to the prior observed data. For example, the data may be normalized.

In one embodiment of the invention, the prior observed data or the discriminating functions obtained from the prior observed data are described with a distribution function. The distribution function can be normal, lognormal, beta, and so forth.

For example, in one embodiment of the invention, the probability density functions (pdfs) for a given sensor for each known source are generated by the Microsoft Excel spreadsheet computer program with NORMDIST(x, µ, σ, 0), where x is the value of interest of a function. µ is the mean and σ is the standard deviation of the sensor data calculated using the spreadsheet functions AVERAGE(range) and STDEV (range). In alternative embodiments of the invention the pdfs for each known source may be generated by constructing a histogram of the data (a plot of frequency versus value for suitably defined ranges) or from the data by the kernel density method. An equivalent function may be used for different spreadsheet computer programs.

In one embodiment the pdfs for the sampled data for none of the known sources are typically generated as a square distribution outside the range of all the observed data for a particular function. It is given an integrated area of 0.9 over a range size equal to the total width of the known sources, with the remaining 0.1 inside the range of the observed data. These limits are set arbitrarily, but the method of the present invention typically is insensitive to the exact values. The pdfs for the sampled data typically indicate that, if the value of a function during operation lies outside the range of all known sources, the probability that it belongs to none of the sources is 0.9. In this case there is a small (0.1) probability that even if a result is located in the range expected the source is still not from one of the known sources.

In a further embodiment of the invention, the probability density functions for each known source and the probability density functions that the sampled data is associated with none of the known sources are normalized.

In one embodiment of the invention the predetermined prior probability is a flat prior probability. In an alternative embodiment of the invention the predetermined prior probability is set according to existing information about the likely source of the data.

In one embodiment of the invention the step of calculating the plurality of respective probabilities that the data are associated with at least one of the known sources or none of the known sources, given the data obtained from a first of the data input sources or sensors, comprises applying Bayesian theory. For each source, the pdf calculated from data obtained by the first of the data input sources or sensors is multiplied with the predetermined prior probability, and the resulting respective products are divided over the sum of all the products for each source. It will be understood that that the term "each source" refers to each and none of the known sources.

Alternatively, for each source, the pdf calculated from the discriminating function related to data sampled by the first of the data input sources or sensors is multiplied with the predetermined prior probability, and the resulting respective products are divided over the sum of all the products for each source.

In another embodiment of the invention the step of calculating a plurality of respective probabilities that the sampled data is associated with at least one of the known sources or none of the known sources, given the data sampled by the first of the data input sources or sensors and a subsequent data input source or sensor, also comprises applying Bayesian theory. For each source, the pdf calculated from data sampled by the subsequent data input source or sensor is multiplied with the respective probabilities calculated in the previous step, and the resulting respective products are divided over the sum of all the products for each source.

Alternatively, for each source, the pdf calculated from the discriminating function related to subsequently sampled data is multiplied with the respective probabilities calculated in the previous step, and the resulting respective products are divided over the sum of all the products for each source.

In one embodiment of the invention the method can be adapted for recognition or identification of the source of the sampled data where the calculated probability that the data sampled with the first and subsequent data input sources or sensors is associated with a known source is equal to or above a threshold probability.

In a second aspect of the invention there is provided a system of determining the probability that data, associated with a source and sampled by a plurality of data input sources, is from a known source, given prior observed data measured by the plurality of data input sources for one or more known sources, the system comprising:
 a) a first calculator for calculating probability density functions for each known source for the sampled data being associated with that source and/or calculating probability density functions for the sampled data not being associated with any one of the known sources using the sampled data and the prior observed data;
 b) a second calculator for calculating a first set of probabilities that the sampled data is associated with at least one of the known sources or none of the known sources using a predetermined prior probability and the probability density functions from step a); and
 c) a third calculator for calculating a subsequent set of probabilities that the sampled data is associated with at least one of the known sources or none of the known sources using the probabilities calculated in step b) and the probability density functions from step a) calculated from the sampled data.

The present invention provides in a third aspect a computer program arranged for determining the probability that data associated with a source and sampled by a plurality of data input sources is from a known source in accordance with the first aspect of the present invention.

In a further aspect of the invention there is provided a computer readable storage medium comprising the computer program as defined above.

In the first, second and third aspects of the present invention the data typically is sampled by detecting molecules conveyed through a gaseous medium emitted from one or more sources. For example, the molecules may be associated with an odour.

In a fourth aspect of the invention there is provided a method of identifying the source of a predetermined type of molecule conveyed through a gaseous medium and sampled by a plurality of sensors, given prior observed data measured by the plurality of sensors in respect of the predetermined type of molecule from one or more known sources, the method comprising the steps of:
 a) calculating probability density functions for each known source that the detected molecules are associated with that source and/or calculating probability density functions for the data being associated with none of the known sources using the sampled data associated with the detected molecules and the prior observed data;
 b) calculating a first set of probabilities that the detected molecules originate from at least one of the known sources or none of the known sources using a predetermined prior probability and the probability density functions from step a);
 c) calculating a subsequent set of probabilities that the detected molecules originate from at least one of the known sources using the probabilities calculated in step b) and the probability density functions from step a); and
 d) assigning a source identity to the sampled data when one of the probabilities calculated in step c) previous step is equal to or above a threshold probability.

The step of assigning the source identity typically comprises assigning the source identity to the sampled data that has the greatest probability.

The present invention provides in a fifth aspect a system for identifying the source of a predetermined type of molecule conveyed through a gaseous medium and sampled by a plurality of sensors, given prior observed data measured by the sensors in respect of the predetermined type of molecule from one or more known sources, comprising:

- a plurality of sensors for detecting the molecules conveyed through the gaseous medium, each sensor being arranged for detecting the molecules of the predetermined type to detect a quantity of the molecules and to produce electronic data associated with the quantity of the molecules; and
- a processor for:
  - a) calculating probability density functions for each known source that the detected molecules originate from that source and/or probability density functions for detected molecules not being associated with any one of the known sources using the sampled data associated with the detected molecules and the prior observed data;
  - b) calculating a first set of probabilities that the detected molecules originate from at least one of the known sources or none of the known sources using a predetermined prior probability and the probability density functions from step a);
  - c) calculating a subsequent set of probabilities that the detected molecules originate from at least one of the known sources or none of the known sources using the probabilities calculated in step b) and the probability density functions from step a); and
  - d) assigning a source identity to the detected molecules when one of the probabilities calculated in step c) is equal to or above a threshold probability.

The processor of the system typically is arranged so that the step of assigning a source identity comprises assigning the source identity to the sampled data that has the greatest probability.

The present invention provides in a sixth aspect a method of determining information about the position of at least one sensor relative to a previously known type of source with which data is associated, the data being relating to a property that is detectable at a plurality of locations and the property being dependent on a distance from the at least one source, the method comprising the steps of:

- obtaining data at the plurality of locations using the at least one sensor;
- determining the probability that the obtained data is associated with a previously known type of source, the probability being calculated for each of the plurality of locations;
- selecting, dependent on the calculated probabilities, at least one previously known type of source; and
- comparing the data for the plurality of locations and from relative differences between the data determining information about a position of the at least one sensor relative to the location of the at least one selected source.

For example, the property may be associated with molecules conveyed through a gaseous medium such as those that relate to an odour that may originate from a sewage plant, a meat processing plant, a chemical plant or the like.

In one embodiment the step of comparing the data comprises determining at least the approximate location of the selected source of the data. For example, the type of source may be known and/or the source may be known, but the location of the source may be unknown. The selected source may be a moving source or may have moved to an unknown location. For example, the source may be positioned on a ship or on another moving object and the source may have emitted molecules that are conveyed through the air and that signal an emergency. The apparatus may then be used to locate the ship or the like.

The step of determining the probabilities that the obtained data is of a previously known type typically comprises use of the method in accordance with the first aspect of the present invention.

The step of comparing the data typically comprises comparing data intensities.

In one embodiment of the present invention the at least one sensor is positioned at each of the plurality of locations.

In another embodiment of the present invention, the at least one sensor moves from one location to another and the data is detected successively. In this case the method typically also comprises, in a feedback loop, estimating a direction or region of the selected source. This step typically is conducted so that the information provided by the feedback loop controls the movement of the at least one sensor so that the at least one sensor moves towards the selected source or away from the selected source.

Moving the at least one sensor may be effected by shifting, driving, flying or otherwise moving the at least one detection system.

The present invention comprises in a seventh aspect an apparatus for determining information about the position of at least one sensor relative to a previously known type of source with which data is associated, the data relating to a property that is detectable at a plurality of locations and the property being dependent on a distance from the at least one source, the apparatus comprising:

- at least one sensor for obtaining the data at the plurality of locations; and
- a system for:
  - determining the probability that the obtained data is associated with a previously known type of source, the probability being calculated for each of the plurality of locations;
  - selecting, dependent on the calculated probabilities, at least one of the previously known type of source; and
  - comparing the data for the plurality of locations and from relative differences between the data determining information about a position of the at least one sensor relative to the location of the at least one selected source.

The system typically comprises the system for determining the probabilities that the obtained data is associated with a previously known source in accordance with the second aspect of the present invention. Further, the system typically is arranged for determining at least the approximate location of the selected source.

For example, the property may be associated with molecules conveyed through a gaseous medium such as those that relate to an odour that may originate from a sewage plant, a meat processing plant, a chemical plant or the like. Each sensor may be a sensor array.

The apparatus may comprise a plurality of sensors arranged for positioning at respective positions.

In another embodiment of the present invention, the at least one sensor is arranged to move from one location to another and the data is detected successively.

The at least one sensor may be arranged for driving, flying or otherwise moving. The at least one sensor may move separately from the system or together with the system. The apparatus may also comprise a transmitter for transmitting information to a base and a receiver for receiving information or a control signal from the base, which may be used for influence of the movement, the data detection or any other property.

The apparatus may be arranged so that the movement is controlled via the feedback loop which is arranged so that the at least one sensor moves towards the selected source.

Alternatively, the apparatus may be arranged so that the movement is controlled via the feedback loop so that the at least one sensor moves away from the selected source.

The system typically comprises a computer and computer software for operation of the method according to the first aspect of the present invention.

The invention will be more fully understood from the following description of specific embodiments of the invention. The description is provided with reference to the accompanying drawings.

DETAILED DESCRIPTION OF SPECIFIC EMBODIMENTS

A method of determining the probability that data from an unknown source, and sampled by an array of sensors, is from a known source, given prior observed data measured by the array of sensors from one or more known sources, is now described with reference to the following illustrative example.

In this specific example the sampled and prior observed data relates to a voltage output from an array of electronic detectors configured to detect predetermined types of molecules conveyed through a gaseous medium. Typically the molecules of the predetermined type result in an airborne odour and comprise organic molecules.

Figure 1:
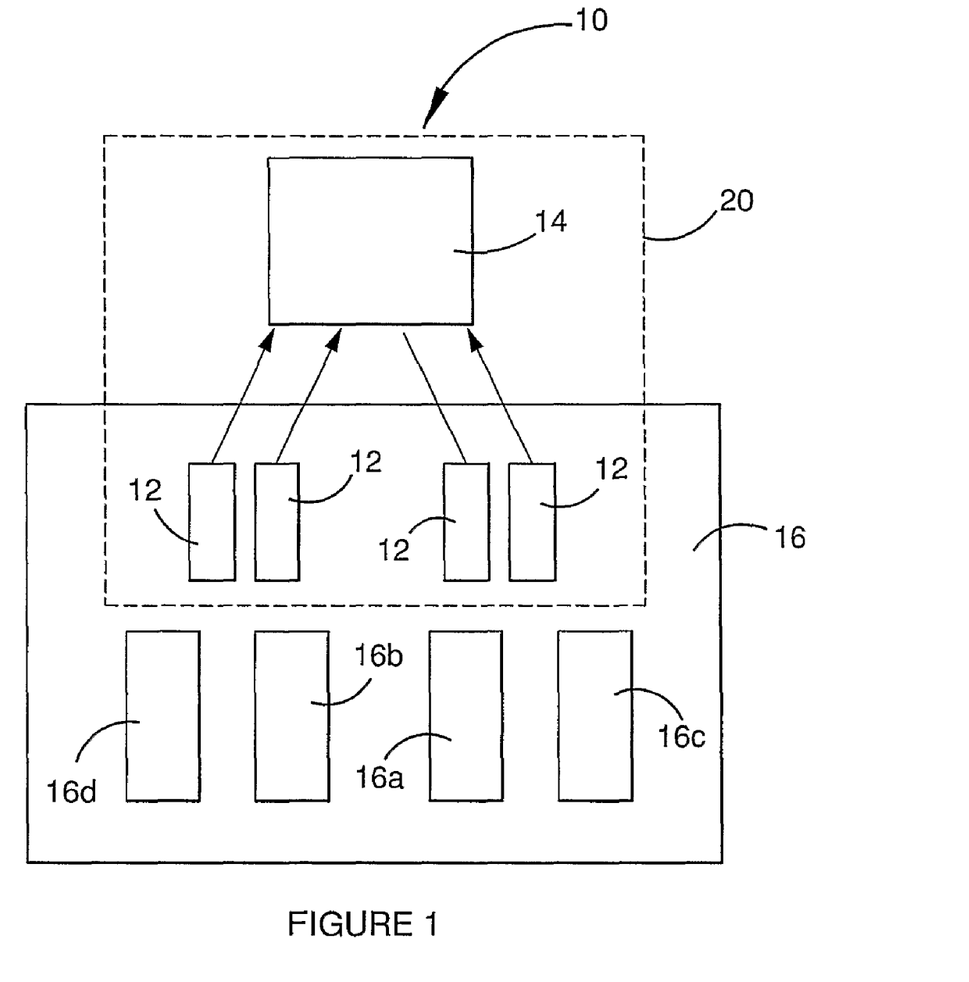
FIG. 1 shows a schematic representation of a system for detecting a predetermined type of molecule conveyed through a gaseous medium.

FIG. 1 shows a schematic representation of a system for detecting a predetermined type of molecule conveyed through a gaseous medium 10. The system 10 comprises one or more detectors 12 and a processor 14. In this embodiment there are four detectors 12 each of which is positioned in proximity of a respective known odour sources 16a, 16b, 16c, and 16d of a plant 16. In a preferred embodiment the processor 14 is a microprocessor or a computer.

The plant can be any source that generates organic molecules entering the environment, thereby causing an odour. For example, the plant may be a sewage plant, a meat producing or livestock processing plant, brewery, chemical plant, oil refinery and so forth. In this embodiment the detectors 12 are multi channel array detectors that comprise an array of five chemical sensors. Each sensor is an odour sensor that has a surface which comprises a receptor for the predetermined type of molecule. When a particular type of odour molecule interacts with a receptor molecule, an electrical property of the sensor surface changes and therefore the odour molecule can be detected. Such multi channel array detectors are also known as an "e-nose" or "electronic nose". Each detector also has a separate detector channel for detecting a temperature and a separate detection channel for detecting humidity.

For example, the detectors 12 may comprise surface acoustic wave sensors, conducting polymer sensors, quartz crystal microbalance sensors, fibre optic sensors, metal oxide sensors.

The detectors 12 are arranged to produce electronic data that is associated with the airborne odour. In this illustrative example the detectors 12, positioned in proximity of known odour sources 16a, 16b, 16c, 16d, are exposed to the airborne odour from the plant 16. The detectors 12 then produce electronic data that is associated with a quantity and type of airborne odour specific to the known sources 16a, 16b, 16c, 16d. The electronic data is directed to processor 14 which is, positioned remote from the detectors 12.

The processor 14 processes the electronic data to provide information about the airborne odour. Additionally, the processor 14 may be adapted to store, accumulate and update information about the airborne odours from respective known sources 16a, 16b, 16c, 16d.

Typically, sensor measurements are taken in predetermined intervals such as every 0.5 seconds and then sequentially converted into electronic data and sent to the processor 14. Prior observed data relating to known sources 16a, 16b, 16c, 16d may be recorded over an extended period (hours, days or weeks) explore natural variation of the odour from that source to be represented in the data. Alternatively, the data may be obtained rapidly. For example the moving device could be programmed to record a strong and/or consistently intense odour, and the processor 14 could then provide the probability of the associated data corresponding to any one of the known sources. If this is not the case, the processor 14 could then be programmed to include that data in a data library and move towards the corresponding source (or away from the corresponding source). The corresponding source that has been located this way could then be included as a known source.

The voltage output from the sensors is averaged to smooth noise. Further, if the sensors are not zeroed (i.e. calibrated to give 0 V in the absence of an odour), it is desirable to subtract the baseline (i.e. the data obtained when there is no odour) from all readings.

Additionally, the voltage output is mathematically manipulated with a discriminating function f(x) to better discriminate among the known odour sources 16a, 16b, 16c, 16d. In this specific example the sensor outputs of sensors 1, 2, 3, and 5 have been divided by the sensor output of sensor 4.

Figure 2:
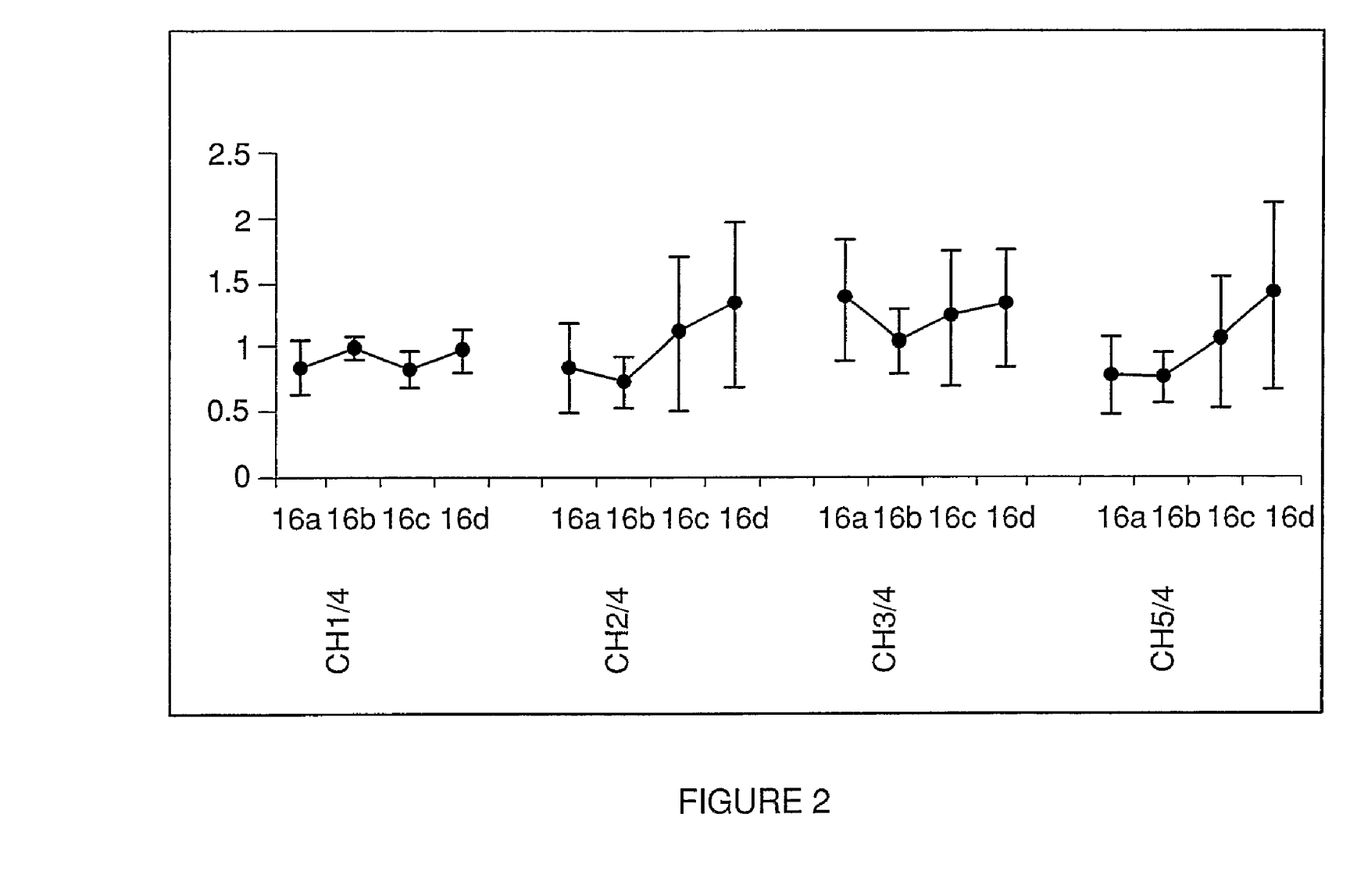
FIG. 2 is a graph of mathematically manipulated representative observed data from four known sources, and sampled by an array of five sensors, showing the average ratios of output data from sensors 1, 2, 3, and 5, respectively to the output data from sensor 4 and standard deviations thereof by location and sensor.

A graph of the average ratios and standard deviations by location and sensor of the prior observed data in this specific example is shown in FIG. 2.

Figure 3:
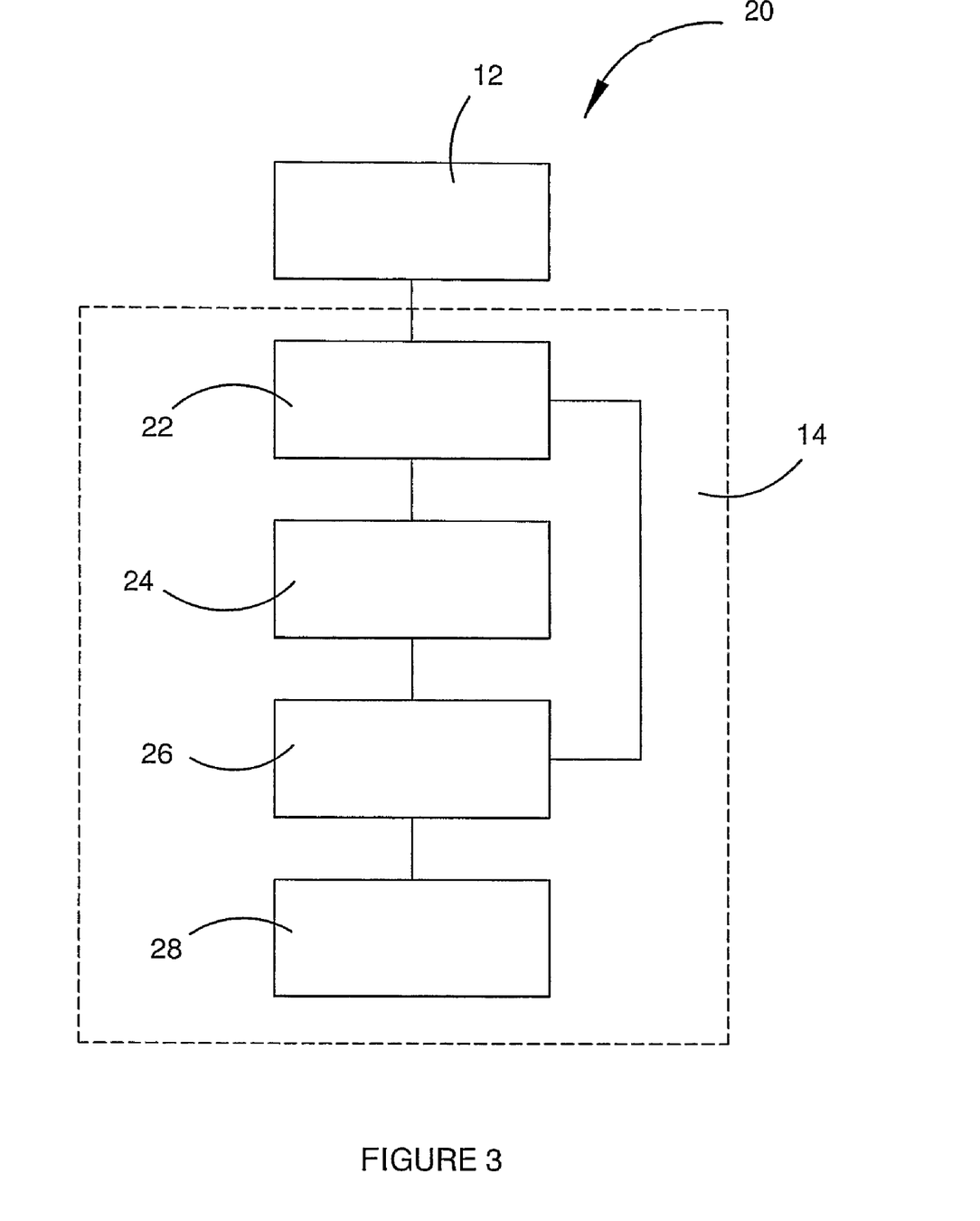
FIG. 3 shows a schematic block diagram illustrating a system according to one embodiment of the invention for determining the probability that data from an unknown source and sampled by an array of sensors is from a known source, given prior observed data measured by the array of sensors from one or more known sources.
Figure 4:
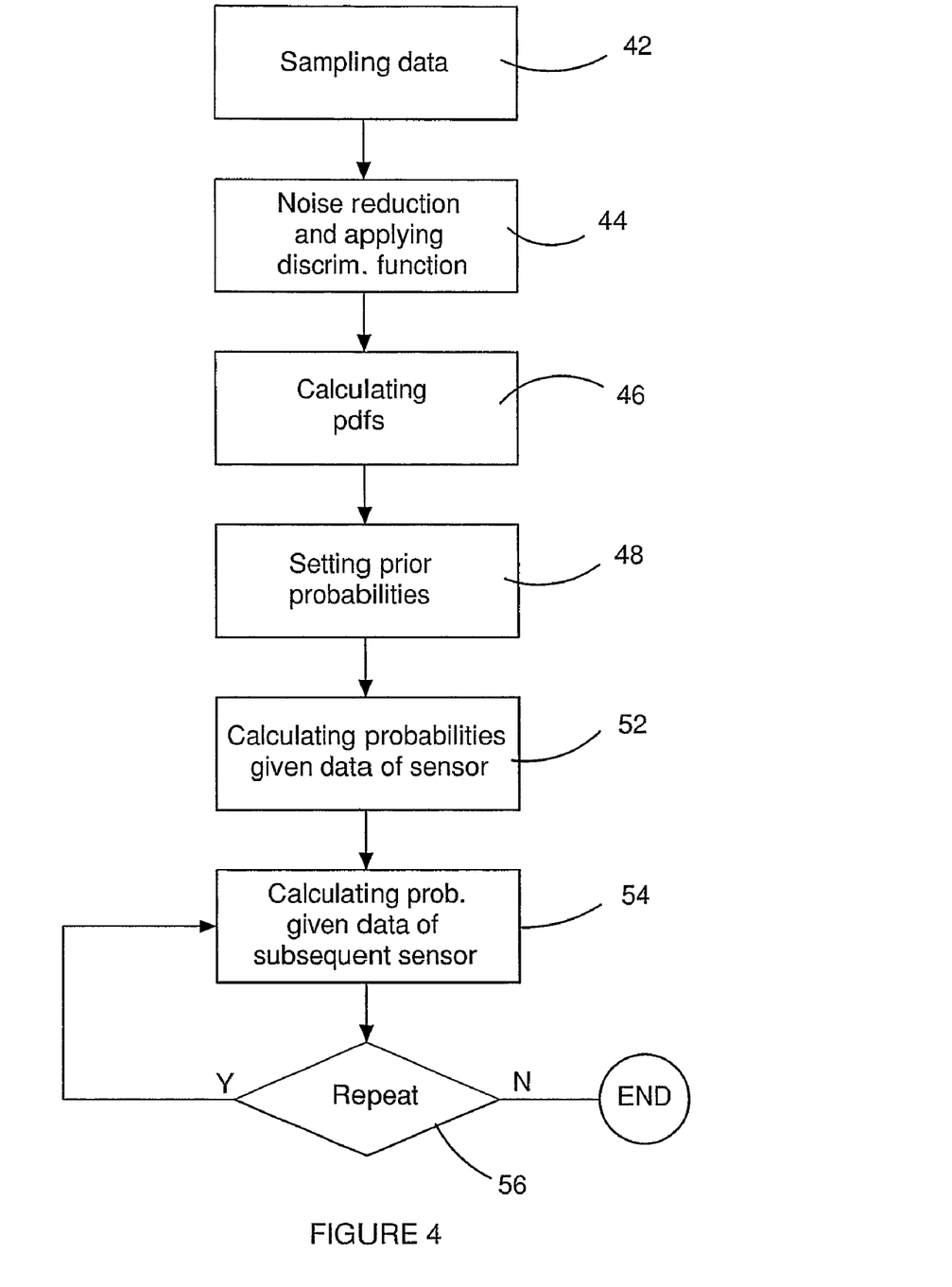
FIG. 4 shows a flow chart illustrating the steps of a method of determining the probability that data from an unknown source and sampled by an array of sensors is from a known source, given prior observed data measured by the array of sensors from one or more known sources, according to one embodiment of the invention.
Figure 5:
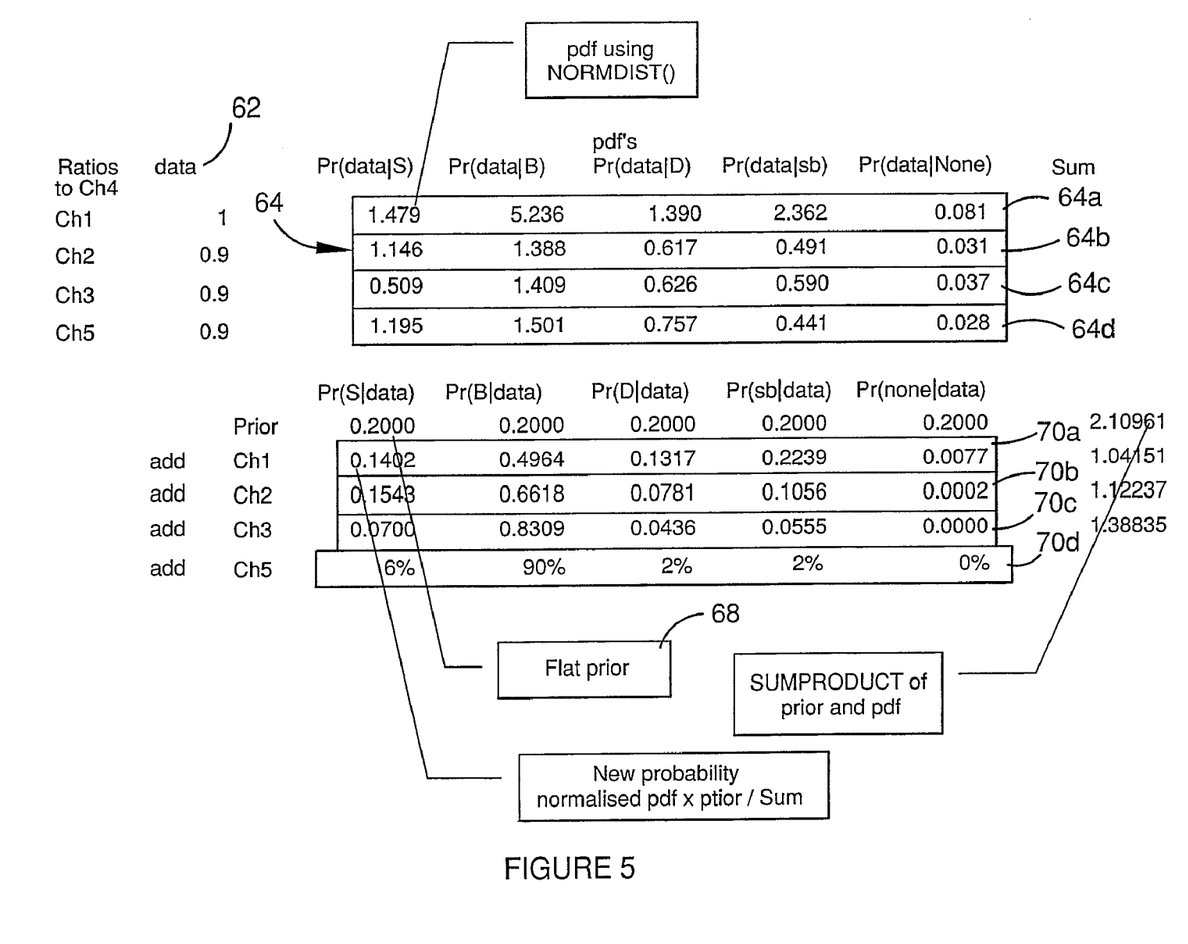
FIG. 5 shows a spreadsheet of representative sampled and prior observed data from four known sources, and sampled by an array of sensors, wherein the sampled and prior observed data have been treated according to a specific embodiment of the method of the present invention.

Referring now to FIGS. 3, 4 and 5, a specific example to illustrate an application of the method of the invention is now described.

FIG. 3 shows a schematic block diagram of a system for identifying the source of a predetermined type of molecule conveyed through a gaseous medium 20. The system 20 includes the detector 12 and the processor 14 described with reference to FIG. 1.

The processor 14 includes a first calculator 22, a second calculator 24, a third calculator 26, and an identity assignor 28.

The first calculator 22 calculates probability density functions for each known source and probability density functions for none of the known sources using the data sampled by the sensors of detector 12 and the prior observed data. It is to be understood that prior to calculating the probability density functions for each source, the first calculator 22 may initially average the sampled data to smooth noise and mathematically manipulate the smoothed data with function f(x). For example, the sensor outputs of sensors 1, 2, 3, and 5 can be divided by the sensor output of sensor 4.

The second calculator 24 calculates a first set of a plurality of respective probabilities that the predetermined type of molecule originates from each one and none of the known sources using a predetermined prior probability and the probability density functions calculated by the first calculator 24 from data sampled by the first of the sensors.

The third calculator 26 calculates a subsequent set of a plurality of respective probabilities that the predetermined type of molecule originates from each one and none of the known sources using the respective probabilities calculated by the second calculator and the probability density functions calculated by the first calculator 24 from data sampled by the subsequent sensor.

It will be understood that the system can include one or more subsequent calculators to calculate a further subsequent set of a plurality of respective probabilities that the predetermined type of molecule originates from each one and none of the known sources using the respective probabilities calculated by the preceding calculator and the probability density functions calculated by the first calculator 24 from data sampled by the further subsequent sensor(s).

The identity assignor assigns a known source identity to the sampled data when one of the respective probabilities calculated by the third calculator 26, or one of the subsequent calculators, is equal to or above a threshold probability.

FIG. 4 shows a flow chart 40 illustrating the steps of a method of determining the probability that data from an unknown source and sampled by an array of sensors is from a known source, given prior observed data measured by the array of sensors from one or more known sources, and FIG. 5 shows a spreadsheet 60 of representative sampled and prior observed data. In the spreadsheet 60 known source 16a is labeled S, known source 16b is labeled B, known source 16c is labeled D, and known source 16d is labeled sb.

Data representing an odour from an unknown source in plant 16, is sampled by sensors 1-5 of the detector 12 (step 42). In step 44 the sampled data is initially averaged to smooth noise and mathematically manipulated with discriminating function f(x) (e.g. the sensor outputs of sensors 1, 2, 3, and 5 have been divided by the sensor output of sensor 4) in the first calculator 22. A representative sample of sampled data ratios 62 is shown for purposes of illustration only in the spreadsheet of FIG. 5.

The sampled data ratios 62 relating to sensors 1, 2, 3, and 5 are then converted in the first calculator 22 to respective probability density functions for each known source 16a, 16b, 16c, 16d and probability density functions for none of the known sources using the prior observed data, as shown in FIG. 2, with NORMDIST in Excel (step 46). A representative sample of respective probability density functions for each known source 16a, 16b, 16c, 16d and probability density functions for none of the known sources 64 is shown for purposes of illustration only in the spreadsheet of FIG. 5.

In the absence of any better information the predetermined prior probabilities 68 are set as 1/N, the so-called "flat prior" (step 48). In this specific example the predetermined prior probabilities 68 are 0.2 for each source.

The respective pdfs for each source for data relating to sensor 1 (64a) are then multiplied with the predetermined prior probabilities 68, in this specific example 0.2, and the resulting respective products are then divided by a product of the predetermined prior probability 68 and the sum of the pdfs from each source for data relating to sensor 1 (step 52).

A mathematical representation of the calculation performed by the second calculator 24 in step 52 is shown below:

$$Pr(16a \mid x_i) = \frac{Pr(x_i \mid 16a)Pr(16a)}{\left[\begin{array}{c} Pr(x_i \mid 16a) + Pr(x_i \mid 16b) + Pr(x_i \mid 16c) + \\ Pr(x_i \mid 16d) + Pr(x_i \mid \text{none}) \end{array}\right] Pr(16a)}$$

where $Pr(x_1 \mid 16a)$ is the pdf from step 46 at function value $x_1$ (e.g. $x_1$ is sensor 1/sensor 4 ratio of 1.479) for known source 16a, and so forth. The result $Pr(16a \mid x_1)$ is read as "the probability of the odour coming from known source 16a, given the function value $x_1$". $Pr(16a)$=predetermined prior probability=0.2.

In step 54 of the method of the present invention, the respective pdfs 64b for each source for data relating to sensor 2 are then multiplied with the respective results 70a of the previous step for each source, in other words $Pr(16a \mid x_1)$, $Pr(16b \mid x_1)$, $Pr(16c \mid x_1)$, $Pr(16d \mid x_1)$, and $Pr(\text{none} \mid x_1)$, replacing the predetermined prior probability 68. The resulting respective products are then divided by a sum of the products of 70a with the respective pdfs 64b from each source for data relating to sensor 2. The results of this calculation in the third calculator 26 are $Pr(16a \mid x_1, x_2)$, $Pr(16b \mid x_1, x_2)$, $Pr(16c \mid x_1, x_2)$, $Pr(16d \mid x_1, x_2)$, and $Pr(\text{none} \mid x_1, x_2)$, which are read as "the respective probabilities of the odour coming from known sources 16a, 16b, 16c, 16d, and none of the known sources given the function value $x_1$ and the function value $x_2$" (70b).

At this stage one can make a decision 56 to cease further calculation, in particular if the probabilities relating to any one of each source has fallen below a low threshold probability so that the source in question can be disregarded as the true source of the odour, or if the probabilities relating to any one of each source is equal to or has risen above a high threshold probability so that the source having the greatest probability can be identified as the true source of the odour.

Conversely, one can continue to iteratively repeat step 54 with the respective pdfs 64c, 64d for each source relating to data obtained by the subsequent sensors 3 and 5 to obtain the respective probabilities of the odour coming from known sources 16a, 16b, 16c, 16d, and none of the known sources given the data from sensors 1, 2 and 3 (70c), and the respective probabilities of the odour coming from known sources 16a, 16b, 16c, 16d, and none of the known sources given the data from sensors 1, 2, 3 and 5 (70d).

It is evident from 70d in the spreadsheet in FIG. 5 that the iterative process of the present invention has significantly discriminated between the available hypotheses for the source of the odour. The probabilities 70d calculated by iteratively repeating step 54 indicate a 90% probability that the odour's source was known source 16b, and with respect to the alternative possible sources, at most only a 6% probability that the odour's source was known source 16a.

Figure 6:
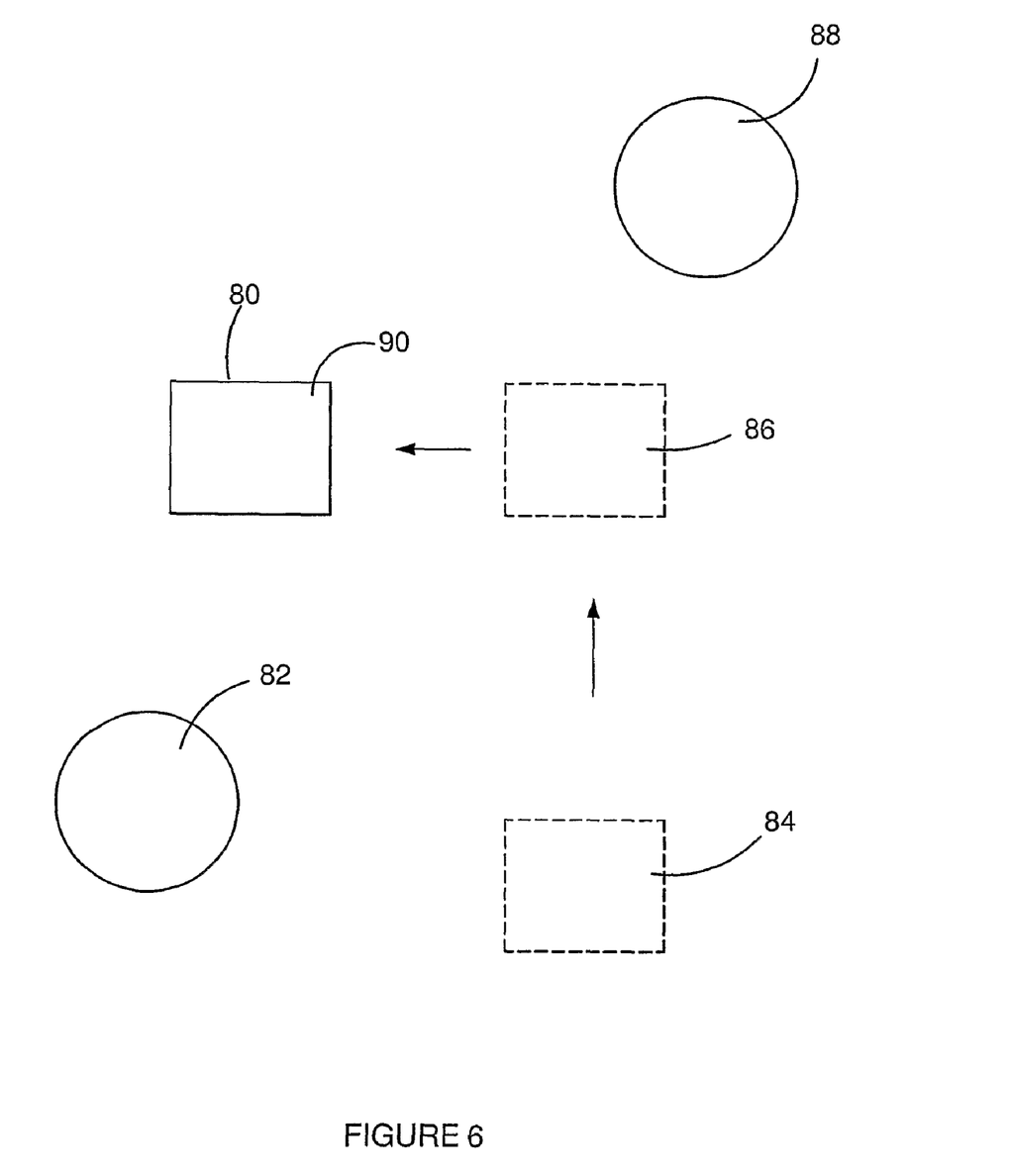
FIG. 6 shows a schematic representation illustrating an apparatus and a method according to an embodiment of the present invention.

Referring now to FIG. 6, an apparatus and a method according to a specific embodiment of the present invention are now described. The apparatus 80 comprises in this embodiment the system 10 for detecting a predetermined type of molecule conveyed through a gaseous medium.

Further, the apparatus 80 comprises the system for determining the probability that data associated with a source and obtained from a plurality of data input sources is associated with a known source. The system is analogous to that described above with reference to FIGS. 3-5.

The apparatus 80 is arranged to obtain data using the system 10. The obtained data is then processed to determine the probabilities that the obtained data is from a previously known source. In this embodiment the apparatus 80 is arranged to detect an odour. The odour may be emitted from a plurality of sources such as source 82. The apparatus 80 is in this embodiment movable relative to the odour sources. Areas 84 and 86 indicate locations of the apparatus 80. When the apparatus 80 is at position 84, data is obtained and the probability for the odour to originate from an odour sources 82 or 88 is calculated. The calculation may have resulted in a high probability for the odour to originate from source 82, in which case the apparatus is set-up to detect changes in intensity associate with that odour. When the apparatus 80 moves to position 86, that intensity reduced as position 86 is located slightly further distant from the odour source 82. The detected change in odour intensities are compared and the apparatus 80 then detects that the position 86 is further away from the source of the order 82 than the position 84.

The apparatus 80 is in this embodiment arranged flying towards the source 82. As the apparatus 80 has detected that the position 86 is further away from the source 82 then the position 84, the apparatus 80 generates a flight path control signal which effects movement of the apparatus 80 towards the source 82 to position 90. At position 90 further data is obtained and the odour intensities are compared and, in a feedback loop, the obtained data is used to control the flight path of the apparatus 80 towards the source 82 whereby the location of the source 82 is identified.

It is to be appreciated that in variations of the described embodiment the apparatus 80 may also be arranged for driving, floating or for any other type of movement. Further, the apparatus 80 may be one of a plurality of apparatus of the same type which are located in the proximity of odour sources and which may not be movable. In this case data obtained by each of the plurality of apparatus is processed and used to identify the location of the odour source 82.

Further, it is to be appreciated that the apparatus 80 may alternatively be directed so that the apparatus 80 moves away from a source of odour. In this case the movement of the apparatus 80 is guided by a decrease in intensity of the data associated with the odour originating from an identified source.

Even though the invention has been described with reference to a particular example it will be appreciated by those skilled in the art that the invention may be embodied in many other forms. For example, the system 10 may comprise any number of detectors 12. Further, each detector 12 may be any type of detector with any number of sensors sensitive to data of any particular type generated by any source.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of determining the probability that sampled data, associated with a source and obtained from a plurality of data input sources, are from a known source, given prior observed data obtained by the plurality of data input sources for one or more known sources, the method comprising the steps of:
   a) calculating probability density functions for each known source for the sampled data being associated with that source and/or calculating probability density functions for the sampled data being associated with none of the known sources using the data and the prior observed data;
   b) calculating a first set of probabilities that the sampled data is associated with at least one of the known sources or none of the known sources using a predetermined prior probability and the probability density functions from step a); and
   c) calculating a subsequent set of probabilities that the data is associated with at least one of the known sources or none of the known sources using the probabilities calculated in the step b) and the probability density functions from step a) calculated from the sampled data:
   wherein the prior observed data is mathematically manipulated to reduce noise or adjust the baseline.

2. The method according to claim 1, wherein the method comprises repeating step c) for a further data set to calculate a further subsequent set of a plurality of probabilities, the further data set having been sampled before, simultaneously or after the sampled data.

3. The method according to claim 1, wherein the method comprises iteratively repeating step c) to calculate further sets of pluralities of probabilities for each of a plurality of further data set obtained before, simultaneously or after the sampled data.

4. The method according to claim 1, wherein the prior observed data is mathematically manipulated according to a discriminating function that is expected to discriminate between known sources of the data ($f/(V)$).

5. The method according to claim 4, wherein the discrimination functions include ratios of data values, logarithms of data values or ratios of data values, performing a principal component analysis (PCA) and taking PC scores, or other linear or non-linear combinations of the data observed with the array of sensors.

6. The method according to claim 4, wherein the data sampled from the source will undergo the same mathematical manipulation as the prior observed data to reduce noise, adjust the baseline for the sampled data, or remove or minimize randomness in the data, and/or to obtain discriminating functions of the data.

7. The method according to claim 4, wherein the prior observed data or the discriminating functions obtained from the prior observed data are described with a distribution function.

8. The method according to claim 7, wherein the distribution function is normal, lognormal, beta.

9. The method according to claim 1, wherein the predetermined prior probability is a flat prior probability.

10. The method according to claim 1, wherein the method can be adapted for recognition or identification of the source of the data whereby the calculated probability that the data obtained from the first and subsequent data input sources originates from a known source is equal to or above a threshold probability.

11. A method of identifying the source of a predetermined type of molecule conveyed through a gaseous medium and sampled by a plurality of sensors, given prior observed data measured by the plurality of sensors in respect of the predetermined type of molecule from one or more known sources, the method comprising the steps of:
   a) calculating probability density functions for each known source that the detected molecules are associated with that source and/or calculating probability density functions for the data being associated with none of the known sources using sampled data associated with the detected molecules and the prior observed data;
   b) calculating a first set of probabilities that the detected molecules originate from at least one of the known sources or none of the known sources using a predetermined prior probability and the probability density functions from step a);
   c) calculating a subsequent set of probabilities that the detected molecules originate from at least one of the known sources using the probabilities calculated in step b) and the probability density functions from step a); and
   d) assigning a source identity to the sampled data when one of the probabilities calculated in step c) previous step is equal to or above a threshold probability.

12. The method of claim 11 wherein the step of assigning the source identity comprises assigning the source identity to the sampled data that has the greatest probability.

13. A system for identifying the source of a predetermined type of molecule conveyed through a gaseous medium and sampled by a plurality of sensors, given prior observed data measured by the sensors in respect of the predetermined type of molecule from one or more known sources, comprising: a plurality of sensors for detecting the molecule conveyed through the gaseous medium, each sensor being arranged for detecting the molecules of the predetermined type to detect a quantity of the molecules and to produce electronic data associated with the quantity of the molecules; and a processor for:
   a) calculating probability density functions for each known source that the detected molecules originate from that source and/or probability density functions for detected molecules not being associated with any one of the known sources using the sampled data associated with the detected molecules and the prior observed data;
   b) calculating a first set of probabilities that the detected molecules originate from at least one of the known sources or none of the known sources using a predetermined prior probability and the probability density functions from step a);
   c) calculating a subsequent set of probabilities that the detected molecules originate from at least one of the known sources or none of the known sources using the probabilities calculated in step b) and the probability density functions from step a); and
   d) assigning a source identity to the detected molecules when one of the probabilities calculated in step c) is equal to or above a threshold probability.

14. The system of claim 13 wherein the processor is arranged so that the step of assigning a source identity comprises assigning the source identity to the sampled data that has the greatest probability.

15. A method of determining information about the position of at least one sensor relative to a previously known type of source with data is associated, the data relating to a property that is detectable at a plurality of locations and the property being dependent on a distance from the at least one source, the method comprising the steps of:
   obtaining data at the plurality of locations using the at least one sensor; determining the probability that the obtained data is associated with the a previously known type of source, the probability being calculated for each of the plurality of locations;
   selecting, dependent on the calculated probabilities, at least one previously known type of source; and
   comparing the data for the plurality of locations and from relative differences between the data determining information about a position of the at least one sensor relative to the location of the at least one selected source of the data;
   wherein the property is associated with molecules conveyed through a gaseous medium.

16. The method of claim 15 wherein the step of comparing the data comprises determining at least the approximate location of the selected source of the data.

17. The method of claim 15 wherein the step of determining the probabilities comprises using the method in accordance with claim 1.

18. The method of claim 15 wherein the step of comparing the data comprises comparing data intensities.

19. The method of claim 15 wherein the at least one sensor is positioned at each of the plurality of locations.

20. The method of claim 15 wherein the at least one sensor moves from one location to another and the data is detected successively.

21. The method of claim 20 wherein moving comprises shifting, driving or flying.

22. The apparatus of claim 21 wherein the at least one sensor is a sensor array.

23. The method of claim 15 comprising, in a feedback loop, estimating a direction or region of the selected source.

24. The method of claim 23 conducted so that information provided by the feedback loop controls the movement of the at least one sensor so that the at least one sensor moves towards the selected source or away from the selected source.

25. An apparatus for determining information about the position of at least one sensor relative to a previously known type of source with which data is associated, the data relating to a property that is detectable at a plurality of locations and the property being dependent on a distance from the at least one source, the apparatus comprising:
   at least one sensor for obtaining data at the plurality of locations; and
   a system for:
      determining the probability that the obtained data is associated with a previously known type of source, the probability being calculated for each of the plurality of locations;
      selecting, dependent on the calculated probabilities, at least one previously known type of source; and
      comparing the data for the plurality of locations and from relative differences between the data determining information about a position of the at least one sensor relative to the location of the at least one selected source of the data;

wherein the property is associated with molecules conveyed through a gaseous medium.

26. The apparatus of claim 25 wherein the system comprises
   a first calculator that calculates a probability density function;
   a second calculator that uses both a predetermined prior probability and the calculated probability density function to calculate a first set of probabilities concerning sampled data; and
   a third calculator that uses both the probability density function and the first set of probabilities to calculate a subsequent set of probabilities concerning the sampled data.

27. The apparatus of claim 25 comprising a plurality of sensors arranged for positioning at respective positions.

28. The apparatus of claim 25 wherein the at least one sensor is arranged to move from one location to another and the data is detected successively.

29. The apparatus of claim 28 wherein the apparatus is arranged so that the movement is controlled via a feedback loop which is arranged so that the at least one sensor moves towards, or away from, the selected source.

30. The apparatus of claim 28 wherein the apparatus is arranged so that the at least one sensor is driven or flown.

* * * * *

UNITED STATES PATENT AND TRADEMARK OFFICE
CERTIFICATE OF CORRECTION

PATENT NO. : 8,255,354 B2
APPLICATION NO. : 12/439334
DATED : August 28, 2012
INVENTOR(S) : Bell et al.

It is certified that error appears in the above-identified patent and that said Letters Patent is hereby corrected as shown below:

On the Title Page, in Item (57), under "ABSTRACT", in Column 2, Line 7, delete "though" and insert -- through --, therefor.

In the Claims

In Column 12, Line 33, in Claim 1, delete "data:" and insert -- data; --, therefor.

In Column 14, Line 13, in Claim 15, delete "the a" and insert -- the --, therefor.

In Column 14, Line 40, in Claim 22, delete "apparatus" and insert -- method --, therefor.

In Column 14, Line 67, in Claim 25, delete "data:" and insert -- data; --, therefor.

In Column 15, Lines 3-4, in Claim 26, delete "comprises" and insert -- comprises: --, therefor.

Signed and Sealed this
Seventh Day of October, 2014

Michelle K. Lee
*Deputy Director of the United States Patent and Trademark Office*